United States Patent
Bair et al.

(10) Patent No.: US 10,947,527 B2
(45) Date of Patent: Mar. 16, 2021

(54) COMPOSITIONS AND METHODS FOR PURIFYING NUCLEIC ACIDS FROM STABILIZATION REAGENTS

(71) Applicant: QIAGEN NORTH AMERICAN HOLDINGS, INC., Germantown, MD (US)

(72) Inventors: Robert Jackson Bair, Plymouth, MN (US); Kim Paulsen, Brooklyn Park, MN (US)

(73) Assignee: QIAGEN North American Holdings, Inc, Germantown, MD (US)

(*) Notice: Subject to any disclaimer, the term of this patent is extended or adjusted under 35 U.S.C. 154(b) by 163 days.

(21) Appl. No.: 16/201,204

(22) Filed: Nov. 27, 2018

(65) Prior Publication Data

US 2019/0345480 A1 Nov. 14, 2019

Related U.S. Application Data

(63) Continuation of application No. 11/265,996, filed on Nov. 3, 2005, now abandoned.

(60) Provisional application No. 60/625,513, filed on Nov. 5, 2004, provisional application No. 60/716,451, filed on Sep. 13, 2005.

(51) Int. Cl.
*C12N 15/10* (2006.01)
*C12Q 1/6806* (2018.01)

(52) U.S. Cl.
CPC ....... *C12N 15/1006* (2013.01); *C12Q 1/6806* (2013.01)

(58) Field of Classification Search
None
See application file for complete search history.

(56) References Cited

U.S. PATENT DOCUMENTS

| | | |
|---|---|---|
| 4,133,753 A | 1/1979 | Takeuchi et al. |
| 4,483,920 A | 11/1984 | Gillespie et al. |
| 4,843,155 A | 6/1989 | Chomczynski |
| 4,870,006 A | 9/1989 | Dragon et al. |
| 4,996,297 A | 2/1991 | Dunbar |
| 5,010,183 A | 4/1991 | Macfarlane |
| 5,057,426 A | 10/1991 | Henco et al. |
| 5,132,207 A | 7/1992 | Kohne et al. |
| 5,155,018 A | 10/1992 | Gillespie et al. |
| 5,234,809 A | 8/1993 | Boom et al. |
| 5,268,526 A | 12/1993 | Hershey et al. |
| 5,346,994 A | 9/1994 | Chomczynski |
| 5,405,951 A | 4/1995 | Woodard |
| 5,422,241 A | 6/1995 | Goldrick et al. |
| 5,480,973 A | 1/1996 | Goodlad et al. |
| 5,496,562 A | 3/1996 | Burgoyne |
| 5,580,970 A | 12/1996 | Hendricks et al. |
| 5,596,092 A | 1/1997 | Schneider |
| 5,599,667 A | 2/1997 | Arnold, Jr. et al. |
| 5,637,687 A | 6/1997 | Wiggins |
| 5,652,141 A | 7/1997 | Henco et al. |
| 5,677,124 A | 10/1997 | DuBois et al. |
| 5,705,382 A | 1/1998 | Endo et al. |
| 5,728,822 A | 3/1998 | Macfarlane |
| 5,773,700 A | 6/1998 | Van Grinsven et al. |
| 5,919,625 A | 7/1999 | Dubois et al. |
| 5,939,259 A | 8/1999 | Harvey et al. |
| 5,939,626 A | 8/1999 | Pasloske et al. |
| 5,945,515 A | 8/1999 | Chomczynski |
| 5,958,677 A | 9/1999 | Lee et al. |
| 5,972,613 A | 10/1999 | Somack et al. |
| 5,973,137 A | 10/1999 | Heath |
| 5,985,572 A | 11/1999 | Macfarlane |
| 5,990,302 A | 11/1999 | Kuroita et al. |
| 6,020,186 A | 2/2000 | Henco et al. |
| 6,037,465 A | 3/2000 | Hillebrand et al. |
| 6,090,593 A | 7/2000 | Fleming et al. |
| 6,123,934 A | 9/2000 | Koyama et al. |
| 6,204,375 B1 | 3/2001 | Lader |
| 6,214,982 B1 | 4/2001 | Pasloske et al. |
| 6,218,531 B1 | 4/2001 | Ekenberg |
| 6,383,393 B1 | 5/2002 | Colpan et al. |
| 6,384,298 B1 | 5/2002 | Krimpenfort et al. |
| 6,399,307 B1 | 5/2002 | Pasloske et al. |
| 6,465,639 B1 | 10/2002 | Van Gemen et al. |
| 6,503,716 B1 | 1/2003 | Lai et al. |
| 6,528,641 B2 | 3/2003 | Lader |
| 6,617,170 B2 | 9/2003 | Augello et al. |
| 6,699,987 B2 | 3/2004 | Hillebrand et al. |
| 6,777,210 B1 | 8/2004 | Pasloske et al. |
| 6,825,340 B2 | 11/2004 | Pasloske et al. |
| 6,855,499 B1 | 2/2005 | Nargessi |
| 7,115,719 B2 | 10/2006 | Paulsen |
| 7,148,343 B2 | 12/2006 | Bair, Jr. et al. |
| 8,598,338 B2 | 12/2013 | Bair et al. |
| 2001/0041332 A1 | 11/2001 | Hillebrand et al. |

(Continued)

FOREIGN PATENT DOCUMENTS

| | | |
|---|---|---|
| JP | 9-327290 A | 12/1997 |
| JP | 2001-526182 A | 12/2001 |

(Continued)

OTHER PUBLICATIONS

Aichi Prefectural Fisheries Experiment Station, *Activity Reports*, pp. 52-53 (1998).
Barrett et al., "High-Quality RNA and DNA from Flow Cytometrically Sorted Human Epithelial Cells and Tissues," *BioTechniques* 32:888-896 (Apr. 2002).
Bugos et al., "RNA isolation from plant tissues recalcitrant to extraction in guanidine," *BioTechniques* 19:734-737 (1995).
Chomczynski et al., "Single-Step Method of RNA Isolation by Acid Guanidinium Thiocyanate-Phenol-Chloroform Extraction," *Analytical Biochemistry* 162:156-159 (1987).
Cox et al., "A single-step procedure for the isolation of individual mRNA species from crude lysates of *Physarum polycephalum*," *FEBS Letters* 155(1):73-80 (May 1983).

(Continued)

Primary Examiner — Katherine D Salmon
(74) Attorney, Agent, or Firm — Seed IP Law Group LLP

(57) ABSTRACT

The invention features reagents, methods and kits for the purification of RNA, or DNA, or both, from a sample.

48 Claims, 3 Drawing Sheets

(56) References Cited

U.S. PATENT DOCUMENTS

| | | |
|---|---|---|
| 2002/0001812 A1 | 1/2002 | Smith et al. |
| 2002/0026046 A1 | 2/2002 | Pasloske et al. |
| 2002/0044919 A1 | 4/2002 | Yu |
| 2002/0106686 A1 | 8/2002 | McKernan |
| 2002/0127587 A1 | 9/2002 | Simms et al. |
| 2002/0150907 A1 | 10/2002 | Fomovskaia et al. |
| 2002/0192689 A1 | 12/2002 | Pasloske et al. |
| 2003/0003465 A1 | 1/2003 | Little et al. |
| 2003/0039985 A1 | 2/2003 | Goldsborough |
| 2003/0073830 A1 | 4/2003 | Heath et al. |
| 2003/0092045 A1 | 5/2003 | Nargessi et al. |
| 2003/0096229 A1 | 5/2003 | Bavykin et al. |
| 2003/0106107 A1 | 6/2003 | Shinozaki et al. |
| 2003/0114651 A1 | 6/2003 | Lader |
| 2003/0157492 A1 | 8/2003 | Heath et al. |
| 2003/0180754 A1 | 9/2003 | Bergholtz et al. |
| 2004/0009496 A1 | 1/2004 | Eiblmaier et al. |
| 2004/0019196 A1 | 1/2004 | Bair, Jr. et al. |
| 2004/0245163 A1 | 12/2004 | Lim et al. |
| 2005/0032105 A1 | 2/2005 | Bair et al. |
| 2005/0059054 A1 | 3/2005 | Conrad et al. |
| 2005/0153292 A1 | 7/2005 | Stordeur et al. |
| 2005/0171333 A1 | 8/2005 | Paulsen |
| 2005/0191760 A1 | 9/2005 | Heath et al. |
| 2006/0099210 A1 | 5/2006 | Cavarec et al. |
| 2006/0251693 A1 | 11/2006 | Short et al. |
| 2006/0276629 A9 | 12/2006 | Hildebrand et al. |
| 2006/0289327 A1 | 12/2006 | Knight et al. |
| 2007/0043216 A1 | 2/2007 | Bair, Jr. et al. |
| 2007/0087369 A1 | 4/2007 | Chen et al. |
| 2007/0091455 A1 | 4/2007 | Bae et al. |
| 2007/0092403 A1 | 4/2007 | Wirbisky et al. |
| 2007/0141583 A1 | 6/2007 | Li et al. |
| 2007/0197771 A1 | 8/2007 | Robinson et al. |
| 2008/0026451 A1 | 1/2008 | Braman et al. |
| 2008/0032285 A1 | 2/2008 | Ebersole et al. |

FOREIGN PATENT DOCUMENTS

| | | |
|---|---|---|
| JP | 2002-187897 A | 7/2002 |
| WO | 92/07863 | 5/1992 |
| WO | 95/01359 | 1/1995 |
| WO | 95/02049 | 1/1995 |
| WO | 2005/058933 | 6/1995 |
| WO | 95/21849 A1 | 8/1995 |
| WO | 95/34569 A1 | 12/1995 |
| WO | 96/18731 A1 | 6/1996 |
| WO | PCT/US99/02189 | 2/1999 |
| WO | 99/13976 | 3/1999 |
| WO | 99/29840 A1 | 6/1999 |
| WO | 00/17320 | 3/2000 |
| WO | 03/033739 | 4/2003 |
| WO | PCT/US01/32073 | 4/2003 |
| WO | 2004/013155 | 2/2004 |
| WO | 2004/094635 | 11/2004 |

OTHER PUBLICATIONS

Dahle et al., "Isolation of RNA from cells in culture using Catrimox-14 cationic surfactant," *BioTechniques* 15:1102-1105 (1993).

Heath et al., "Apparatuses and Methods for Isolating Nucleic Acid," U.S. Appl. No. 09/154,830, filed Sep. 17, 1998.

Hofmeister, "On the theory of the effects of salts," *Arch. Exp. Pathol. Pharmakol. (Leipzig)* 24:247-260 (1888). Full translation.

Jobes et al., "Plant DNA Isolation," *Taxon* 44:379-386 (1995).

Kondo et al., "Rapid isolation of plasmid DNA by LiCl-ethidium bromide treatment and gel filtration," *Analytical Biochemistry* 198:30-35 (1991).

Krawetz et al., "Isolation and fractionation of total nucleic acids from tissues and cells," Journal of Biochemical and Biophysical Methods 12:29-36 (1986).

Lemarchand et al., "Optimization of microbial DNA extraction and purification from raw wastewater samples for downstream pathogen detection by microarrays," *Journal of Microbiological Methods* 63:115-126 (2005).

Lin et al., "DNA Sequence Analysis of a Complementary DNA for Cold-Regulated *Arabidopsis* Gene cor15 and Characterization of the COR15 Polypeptide," *Plant Physiol.* 99:519-525 (1992).

McFarlane et al., "Isolating RNA from Clinical Samples with Catrimox-14 and Lithium Chloride," *J Clin Lab Anal.* 11:132-139 (1997).

Pirttila et al., "DNA Isolation Methods for Medicinal and Aromatic Plants," *Plant Molecular Biology Reporter* 19:273a-273f (2001).

Sigma Aldrich Biological Buffers www.sigmaaldrich.com.

Stordeur et al., "Immune monitoring in whole blood using real-time PCR," *Journal of Immunological Methods* 276:69-77 (2003).

Surzycki "General Aspects of DNA Isolation and Purification," *Springer-Verlag GMBH and Co. KG, Berlin*, 1-32 (2000).

Technical Bulletin #160: The Use of LiCl Precipitation for RNA Purification, URL = http://www.ambion.com/techlib/tb/tb_160.html (downloaded May 22, 2003).

Thach et al., "Assessment of two methods for handling blood in collection tubes with RNA stabilizing agent for surveillance of gene expression profiles with high density microarrays," *Journal of Immunological Methods* 283:269-279 (2003).

Witchel et al., "Milligram quantity preparation of RNA from a marine invertebrate with a high fluid content," *BioTechniques* 21:1024-1026 (1996).

FIG. 1

| RNA Isolation from Tempus RNA tube | RNA Isolation from PAXgene RNA tube | DNA Isolation from PAXgene RNA tube |
|---|---|---|
| Collect blood sample, mix, store as recommended by manufacturer ||| 
| Add 3mL Ethanol<br>Vortex<br>Centrifuge<br>Decant | Centrifuge<br>Wash Pellet 5mL Water<br>Centrifuge<br>Decant ||
| | Add 100-200 µL Resuspension Buffer ||
| | | Add 2 µL RNase (Optional)<br>Incubate 5 min RT |
| Add 200-300 µL Lysis Solution |||
| | Add 10 µL Proteinase K ||
| | Incubate 0°C 15 min ||
| | | Add > 300 µL Binding Buffer or Wash 1 |
| Add to binding column |||
| Add 400 µL Wash 1 || Optional: Add 400 µL Wash 1 |
| Add 50 µL DNase |||
| Add 200 µL DNAse Wash |||
| Add 200 µL DNAse Wash |||
| Add 200 µL Wash 2 |||
| Add 200 µL Wash 2 |||
| Elute in Water, DEPC treated Water, or 10mM Tris/0.1mM EDTA || Elute in TE |

COMPOSITIONS AND METHODS FOR PURIFYING NUCLEIC ACIDS FROM STABILIZATION REAGENTS

CLAIM OF PRIORITY

This application is a continuation of U.S. application Ser. No. 11/265,996, filed on Nov. 3, 2005, which claims priority to U.S. Application No. 60/625,513 filed on Nov. 5, 2004, and U.S. Application No. 60/716,451 filed on Sep. 13, 2005. U.S. application Ser. Nos. 11/265,996, 60/625,513, and 60/716,451 are herein incorporated by reference in their entity.

TECHNICAL FIELD

This invention relates to materials and methods for isolating RNA, DNA, or both, from a sample.

BACKGROUND

Nucleic acids such as deoxyribonucleic acid (DNA) and ribonucleic acid (RNA) are used extensively in the field of molecular biology for research and clinical analyses. A number of methods exist for isolating DNA and RNA from biological samples, which entail disruption of cells and liberating nucleic acids into a solution. RNA is highly sensitive to degradation. Therefore, methods also exist for protecting RNA from enzymatic digestion by RNA degrading enzymes (e.g., RNases). The RNA can then be separated from the DNA, protein, and other contaminants. These isolation processes are usually performed in a stepwise fashion, wherein cells are lysed under conditions that inhibit RNase activity, followed by further purification, in separate steps. Methods have also been developed to stabilize RNA at the point of collection to permit storage of the sample prior to further purification of the RNA.

Current nucleic acid stabilization product systems allow for only limited purification options. For example, these stabilization product systems and their reagents restrict users to purification products specially designed by the manufacturer of the collection tube. The methods are limited in their versatility in that they either require dedicated capital equipment, are difficult to use, or are limited in the ability to isolate both RNA and DNA from the same sample. Therefore, users need to choose a "stabilization" tube for RNA or DNA and are required to purchase separate nucleic acid isolation kits for each.

SUMMARY

Formulations and methods featured by the present invention allow for the extraction and purification of RNA, or DNA, or both, from the same sample, thus providing an advantage to users. Additionally, formulations and methods featured by the present invention can be used with collection tubes from many manufacturers, thus providing a simple, flexible, and cost-effective solution for the user, regardless of the collection tube they choose.

With the development of collection tubes and reagents for preservation and stabilization of nucleic acid in biological samples, methods are needed that allow end users options to effectively isolate RNA, or DNA, or both, from the same sample. Currently, a user must purchase separate kits and separate collection tubes for DNA and RNA. There are several methods commercially available for the preservation or stabilization of samples. However, no materials and methods, nor kits, are available that allow for the extraction of both DNA and RNA from the same tube.

The present invention provides a method for isolating RNA from a test sample containing RNA involving preparation of a crude lysate from a stabilized sample, contacting the crude lysate with a Solubilization Solution comprising a buffer at a pH between about 7 and 9, a base, an amphiphilic reagent; contacting the sample with a Lysis Solution buffered at a pH of greater than about 7 to create an isolation sample, wherein the Lysis Solution comprises a complexing salt; contacting the isolation sample to a solid support such that nucleic acids comprising substantially undegraded RNA in the isolation sample bind to the solid support; washing the solid support with one or more Wash Solutions to remove materials other than bound nucleic acids comprising substantially undegraded RNA; and eluting the bound substantially undegraded RNA from the solid support in order to obtain substantially pure and undegraded RNA.

The present invention also provides a method for isolating DNA from a test sample containing DNA involving preparation of a crude lysate from a stabilized sample, contacting the crude lysate with a Solubilization Solution comprising a buffer comprising a buffer at a pH between about 7 and 9, a base, an amphiphilic reagent; contacting the sample with a Lysis Solution buffered at a pH of greater than about 7 to create an isolation sample, wherein the Lysis Solution comprises a complexing salt; contacting the isolation sample with either (i) a Binding Solution comprising a buffer, a lithium salt, and an amphiphilic reagent, or (ii) a wash solution comprising a lithium salt and an alcohol to create a binding sample; contacting the binding sample to a solid support such that nucleic acids comprising substantially undegraded DNA in the binding sample bind to the solid support; washing the solid support with one or more Wash Solutions to remove materials other than bound nucleic acids comprising substantially undegraded DNA; and eluting the bound substantially undegraded DNA from the solid support in order to obtain substantially pure and undegraded DNA.

The present invention further provides a method for isolating both DNA and RNA from a sample involving dividing the sample into a first and second tube (or dividing the sample after the Solubilization Solution is added to the sample); isolating the RNA from the sample in the first tube according to the RNA isolation method described above; and isolating the DNA from the sample in the second tube according to the DNA isolation method described above.

The present invention also provides a method for isolating substantially pure and undegraded RNA from a test sample containing RNA. The method involves contacting the test sample stabilized with a guanidinium stabilizing agent, such as the Tempus™ stabilizing agent (see, e.g., U.S. Pat. No. 5,972,613 and WO 99/29840) with an alcohol; centrifuging the test sample to form a crude lysate pellet and a supernatant; removing the supernatant; contacting the crude lysate pellet with a Lysis Solution buffered at a pH of greater than about 7 to create an isolation sample, wherein the Lysis Solution comprises a complexing salt; contacting the isolation sample to a solid support such that nucleic acids comprising substantially undegraded RNA in the isolation sample bind to the solid support; washing the solid support with one or more Wash Solutions to remove materials other than bound nucleic acids comprising substantially undegraded RNA; and eluting the bound substantially undegraded RNA from the solid support in order to obtain substantially pure and undegraded RNA. Alcohols that can be used in this process can be either ethanol or methanol or a combination of methanol and ethanol. The alcohol is present in a concentration of between about 30% and 100%, or between 70% and 95%. It should be noted that when the supernatant is removed from the test sample after the centrifuging step, the guanidinium from the stabilizing agent is substantially removed, so that the crude lysate pellet is substantially free of guanidinium. The term "substantially free of" means that less than 1% (e.g., less than 0.5% or 0.1%, or even less than 0.01%) of the original starting volume of the stabilizing agent is present in the crude lysate. Any residual guanidinium that may remain will not have an impact on the chemistry of subsequent purification processes.

The present invention provides a formulation for solubilizing a material containing nucleic acids, where the formulation contains Tris-HCl at a concentration of about 10 to 20 mM and at a pH between about 7 and 9, Tris base at a concentration of about 20 to 50 mM, Triton-X at a concentration of about 5 to 15%, and EDTA at a concentration of about 1 to 20 mM.

The present invention provides a kit for isolating RNA, DNA, or both, which comprises packaging, containing (separately packaged) a Solubilization Solution, a Lysis Solution, a Wash I Solution or Binding Solution, a Wash II Solution, and a protocol for isolation of RNA, DNA, or both, from a sample.

Other features and advantages of the invention will be apparent from the following detailed description, and from the claims. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. The disclosed materials, methods, and examples are illustrative only and not intended to be limiting. Skilled artisans will appreciate that methods and materials similar or equivalent to those described herein can be used to practice the invention.

BRIEF DESCRIPTION OF THE FIGURES

FIG. 1 is a flow diagram depicting the procedure one would use to isolate DNA, RNA, or both, from a sample collected in PAXgene Blood RNA collection tubes or to isolate RNA from a sample collected in Tempus Blood RNA collection tubes using the present invention.

DETAILED DESCRIPTION

Nucleic Acid Purification or Isolation

Figure 2:
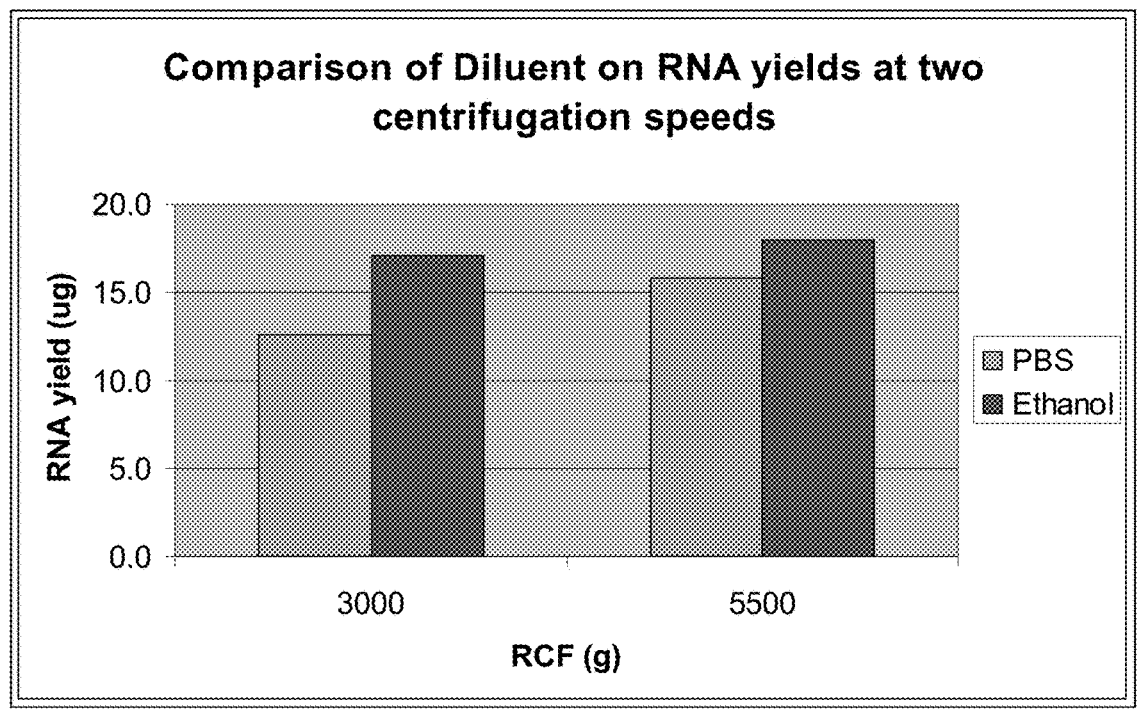
FIGS. 2-4 illustrate the effect of using different diluents and centrifugation conditions for the preparation of a crude lysate from a Tempus Blood RNA collection tube.

Developments in the biological, medical and pharmacological sciences have increased the interest in studying genes, and have intensified the need for sophisticated methods to obtain nucleic acids from a variety of samples. For example, ribonucleic acids provide extensive information of the genetic origin and the functional activity of cells. Such information can be used, for example, in clinical practice, to diagnose infections, detect the presence of cells expressing oncogenes, detect heredity disorders, monitor the state of host defense mechanisms, investigate and diagnose metabolic diseases, investigate influence of drugs on gene expression in patients, and investigate side and toxic effects of drugs.

Numerous nucleic acid purification methods exist that fall into two general categories, liquid phase purification and solid phase purification. In liquid phase purification, nucleic acids remain in the liquid phase, while impurities are removed by precipitation and/or centrifugation. Alternatively, nucleic acids are precipitated out while the impurities remain. In solid phase purification, the nucleic acids are bound to a solid support, while impurities are selectively eluted. For example, RNA isolated by liquid phase purification remains in the liquid phase, while impurities are removed by processes such as precipitation and/or centrifugation. In solid phase purification, RNA is bound to a solid support while impurities such as DNA, proteins, and phospholipids are selectively eluted. Both purification categories aim at yielding substantially undegraded RNA. Both purification strategies utilize conventional methods, which require numerous steps and, often, hazardous reagents, as well as more rapid methods, which require fewer steps and usually less hazardous reagents. In the case of RNA purification, if the starting material (e.g., biological material) includes cells, both the liquid and solid methods require a cell or viral co-rupture, or a lysis step. A rupture, or lysis, step results in RNA mixed with contaminants such as DNA, lipids, carbohydrates, proteins, etc. Such a mixture also contains RNases that degrade RNA and must be removed and/or inactivated, so as to not interfere with yielding substantially undegraded RNA.

Traditionally, liquid phase RNA isolation methods have used liquid-liquid extraction (i.e., phenol-chloroform) and alcohol precipitation. One commonly used liquid-liquid RNA extraction method is the "acid-guanidinium-phenol" method of Chomczynski and Sacchi (Chomczynski P., Sacchi N., Single-step method of RNA isolation by acid guanidinium thiocyanate-phenol-chloroform extraction, *Anal Biochem* 162: 156-9 [1987]; U.S. Pat. Nos. 5,945,515, 5,346,994, and 4,843,155). This method includes: (1) extracting a sample with a guanidinium isothiocyanate (GITC) solution to which an acidic medium, phenol, and chloroform are added consecutively; (2) centrifuging the mixture to separate the phases, such that the proteins denatured by the phenol may be removed from the nucleic acids that are found in an intermediate layer; (3) adding an alcohol so as to precipitate, and thereby concentrate the RNA; and (4) washing and re-hydrating the purified RNA. Although this method has been demonstrated to ensure the purification of RNA, it utilizes hazardous reagents such as chloroform and phenol, is labor intensive, and subject to carryover of the organic reagents into the purified sample.

Precipitation of nucleic acids by cationic detergents is another example of liquid phase technology (U.S. Pat. Nos. 5,985,572; 5,728,822 and 5,010,183 (MacFarlane)). For example, U.S. Pat. No. 5,985,572 discloses a method for isolating RNA from biological samples using selected quaternary amine surfactants. A non-hazardous liquid phase purification method was disclosed by Heath (U.S. Pat. No. 5,973,137) using low pH lysing and precipitation reagents. However, liquid phase methods have serious disadvantages in that they involve tedious precipitation steps, and are consequently difficult to automate. Thus, the need for high-throughput RNA purification has led to the development of solid phase methods. In some embodiments, RNA isolation involves homogenizing cells in guanidinium isothiocyanate, followed by sequential addition of sodium acetates and phenol, and chloroform/isoamyl alcohol. Some methods for lysing cells and inhibiting RNases are known that use chaotropic salts of guanidinium. After centrifugation, RNA is precipitated from the upper layer by the addition of alcohol. Other methods include the addition of hot phenol to a cell suspension, followed by alcohol precipitation. These methods are hazardous to the user, and disposal of the reagents that are used can be costly.

Substantially undegraded DNA can be isolated by a variety of liquid and solid phase methods known to those having ordinary skill in the art. For example, DNA can be isolated by routine techniques such as described in Maniatis et al., 1989 (in Molecular Cloning, A Laboratory Manual, Cold Springs Harbor Laboratory, NY), or in Persing et al. (eds.) (1993), Diagnostic Molecular Microbiology: Principles and Applications (American Society for Microbiology, Washington D.C.).

For solid phase DNA purification, many solid supports have been used including membrane filters, magnetic beads, metal oxides, and latex particles. Probably the most widely used solid supports are silica-based particles (see, e.g., U.S. Pat. No. 5,234,809 (Boom et al.); International Publication No. WO 95/01359 (Colpan et al.); U.S. Pat. No. 5,405,951 (Woodard); International Publication No. WO 95/02049 (Jones); WO 92/07863 (Qiagen GmbH). For example, the method disclosed in U.S. Pat. No. 5,234,809 (Boom et al.) uses a high concentration chaotropic solution to bind DNA to silica particles and requires six centrifugation steps and five reagents to purify DNA from whole blood. Disadvantages of this method are the use of a particulate suspension, the use of many centrifugation steps, and the use of hazardous reagents, such as guanidinium isothiocyanate and acetone.

In another example, U.S. Pat. No. 5,496,562 (Burgoyne) describes a method of purifying cellulose filter paper containing dried blood that uses four reagents during four phenol washes and five isopropanol washes. After drying, a small piece of the filter paper is cut from the square and used directly as a substrate for PCR amplification. Despite the use of bound DNA for analysis, these methods still require many steps and hazardous reagents.

Samples

Samples, such as biological samples, can be collected by a variety of means. For example, sample collection containers are used for collecting and storing samples. In some embodiments, collection containers are glass or plastic tubes having a resilient stopper. In other embodiments, blood collection tubes are used, where the tube is evacuated to draw a volume of blood into the tube. In some embodiments, collection tubes can have various additives, such as ethylenediaminetetraacetic acid (EDTA) contained therein, in order to prepare the blood sample for a particular test. In other embodiments, the additive is an anticoagulation agent. In some instances, the anticoagulation additive is a buffered citrate or heparin in an aqueous solution. In other instances, the aqueous citrate is combined with the blood sample in a specified amount to determine the amount of an anticoagulant needed for conducting certain tests. Such treated collection tubes, however, are used mainly for serological testing, since the additives do not stabilize nucleic acids in the sample.

Sample-collection containers are used for collecting and/or storing a variety of samples. In certain embodiments, sample collection containers are used to collect and/or store biological fluids or samples (e.g., whole blood, bone marrow, blood spots, blood serum, blood plasma, buffy coat preparations, saliva and cerebrospinal fluid, buccal swabs, cultured cells, cell suspensions of bacteria, solid animal tissues such as heart, liver and brain, body waste products, such as feces and urine, environmental samples taken from air, water, sediment or soil, plant tissues, yeasts, bacteria, viruses, mycoplasmas, fungi, protozoa, rickettsia, and other small microbial cells). In other embodiments, sample collection containers are used to collect and/or store lysates, homogenates, or partially purified samples of biological materials. In other instances, biological materials include crude or partially purified mixtures of nucleic acids.

Several commercial products, which have been introduced in recent years, preserve a biological sample (e.g., blood) in collection tubes, and also "stabilize" the nucleic acids. "Stabilization" is particularly useful to protect RNA from degradation, and to allow for a sample to be stored for later purification of nucleic acids. PreAnalytiX™ (Valencia, Calif.) offers blood collection tubes for stabilization of DNA or RNA (U.S. Pat. No. 6,617,170). The trade name of these tubes is Paxgene™ DNA collection tubes, and Paxgene™ RNA collection tubes. These tubes use a formulation of tetradecyl-trimethylammonium oxalate and tartaric acid. The Paxgene™ Blood Tube is a plastic, evacuated tube used for the collection of whole blood, and stabilization of RNA in the blood sample. PreAnalytix™ additionally offers separate kits for the purification of either DNA or RNA from these collection tubes.

Applied Biosystems (Foster City, Calif.) markets and sells blood collection tubes for the stabilization of RNA. The trade name of these tubes is Tempus™ RNA collection tubes. These tubes use a formulation containing guanidine hydrochloride. This product's solution stabilizes total RNA from whole blood for up to five days at room temperature. Ambion (Austin, Tex.) offers a reagent for RNA stabilization (U.S. Pat. No. 6,528,641). The trade name of this reagent is RNAlater® solution. This reagent uses a formulation of ammonium sulfate. RNAlater® is an aqueous tissue and cell storage reagent that stabilizes and protects cellular RNA in intact, unfrozen tissue, and cell samples. RNAlater® eliminates the need to immediately process samples or to freeze samples in liquid nitrogen for later processing. A user cuts tissue samples to be stored, so they are less than 0.5 cm in at least one dimension, and submerges them in five volumes of RNAlater® until they are ready to purify the nucleic acids from the sample.

Omega Bio-Tek markets and sells a reagent for stabilization of RNA. The trade name of this reagent is RNAsafer® Stabilizer Reagent. Once this reagent is applied to a sample, it penetrates cells and tissues, and inactivates RNases at room temperature. Samples can be stored in RNAsafer® Stabilizer Reagent for up to 12 months at −20° C.

Methods of the Invention

Reagents

The present invention features several categories of reagents: Diluent Solution, Solubilization Solution, Lysis Solution, Proteinase K Solution, Binding Solution, Wash Solutions, and Elution Solutions.

(i) Diluent Solution:

In some embodiments a diluent is added to a biological material in the presence of a stabilizing agent to facilitate the preparation of a crude lysate. The manufacturer of Tempus™ solutions (Applied Biosystems, Inc.) specifies that PBS be used. The PAX system does not require a Diluent solution. In one embodiment described in Example 4 below, alcohol was used to improve robustness of the process.

(ii) Solubilization Solution:

A Solubilization Solution is used to solubilize a sample pellet following centrifugation to generate a crude lysate. In some embodiments, the Solubilization Solution formulation includes a buffer, a base, an amphiphilic reagent, such as a detergent or surfactant or mixture thereof, and an optional chelator. For example, the Solubilization Solution may contain a buffer, such as Tris HCl, at a pH between 7-9 (e.g., pH 7.1, 7.3, 7.5, 7.8, 8.0, 8.2, 8.6, 8.8, 8.9, or 9). In some embodiments, the buffer concentration may be at 10-20 mM (e.g., at 10.5 mM, 11 mM, 11.7 mM, 12 mM, 12.5, mM, 13 mM, 13.6 mM, 14 mM, 14.2 mM, 14.8 mM, 15 mM, 16 mM, 17 mM, 18 mM, 19 mM, or 19.5 mM). A base concentration may be at 20-50 mM (e.g., Tris base at 21 mM, 25 mM, 27 mM, 31 mM, 35 mM, 38 mM, 42 mM, 47 mM, or at 49 mM). In some instances, the Solubilization Solution may additionally include an amphiphilic reagent. An amphiphilic reagent includes a compound or a molecule having a hydrophilic group attached to a hydrophobic functionality, such as a hydrocarbon chain, and having surfactant properties. In some instances, the amphiphilic reagent is a detergent. Anionic, cationic, and zwitterionic detergents may be used. In certain instances, a non-ionic detergent is used in nucleic acid isolation. In other embodiments, non-ionic detergents from the Tween class are used (e.g., Tween-20, Tween-40, Tween-60, Tween-80, etc.). In some instances, Triton class detergents are used (e.g., X-100, X-114, XL-80N, etc). In other instances, Tergitols (e.g., XD, TMN-6), Nonidets or Igepal (e.g., NP-40) detergents are used. In some embodiments, the nonionic detergent is used at a concentration of 5-15% (e.g., Triton-X at about 5%, 7%, 8%, 10%, 12%, or 14%). In other embodiments, the chelating agent ethylenediaminetetraacetic acid (EDTA) is added at a concentration of 1-20 mM (e.g., at 5-10 mM, 6-9 mM, 7-8 mM, 8 mM, or 7.5 mM)

(iii) Lysis Solution:

A Lysis Solution enables efficient lysis (e.g., of cells in a biological sample) to release nucleic acids, effectively inhibits nucleic acids-degrading enzymes' activity, and allows nucleic acids to bind to a solid support of choice. A Lysis Solution of the present invention contains a buffer (such as Tris-HCl), an alkali-metal salt (such as Sodium salts, for example sodium chloride, or Lithium salts, for example lithium chloride or lithium bromide), an amphiphilic reagent (such as a detergent, or surfactant, or a mixture thereof), and optionally chelating reagents (such as EDTA or CDTA). A Lysis Solution of the present invention is unique in that it requires no added strong chaotropic substances such as guanidinium salts, urea, etc. Guanidinium salts and urea are strong chaotropic salts that disrupt the structure of water and thus tend to decrease the strength of hydrophobic interactions resulting in a drastic effect on other solute molecules. For example, urea, when dissolved in water, disrupts the secondary, tertiary, and quaternary structures of proteins, and subsequently causes dissociation of proteins from RNA. Guanidinium salts and urea dissolve in water through endothermic reactions. Both guanidinium salts and urea are considered to be strong chaotropic salts as defined by the Hofmeister series, a widely used system that ranks cations and anions according to relative chaotropic strength (F. Hofmeister, On the understanding of the effects of salts, *Arch. Exp. Pathol. Pharmakol.* (Leipzig) 24 (1888) 247-260).

Unlike strong chaotropic salts, the reaction of alkali-metal salts, (e.g., sodium chloride, lithium chloride and lithium bromide) in water is an exothermic reaction and is indicative of the tremendous ion-dipole interaction exhibited by the strong kosmotropic lithium ion and the resulting large solubility. Differences such as these are indicative of the differences between the strong chaotropic substances, such as guanidinium salts, and the alkali-metal salts, especially lithium chloride, of the present invention.

A first component of the Lysis Solution is a buffer that maintains the pH of the solution (e.g., a Tris buffer or any known buffer). For example, the pH of the buffer may be at least about 8, at least about 8.5, or even at least about 9 (e.g., 8.1, 8.4, 8.6, 8.7, 8.9, 9.1, or 9.5). The buffer may have a pKa of at least about 8 (e.g., 8.1, 8.3, 8.5, 8.6, 8.8, or 8.9), and may be used at a concentration of 50-150 mM (e.g., 60 mM, 70 mM, 80 mM, 90 mM, 100 mM, 120 mM, or 140 mM). In some embodiments, Tris buffer is an appropriate buffer. In some instances, Tris buffer with a pH of 8.0 and a concentration of 100 mM is used. In some other embodiments, a base may be used to adjust the pH of the Lysis Solution. The base may be one that can raise the pH of the solutions to no less than 7 (e.g., pH 7.5, 8, 8.5, or 9.0). In some instances, the base may be an alkali-metal hydroxide. Such alkali-metal hydroxides include, but not limited to, sodium hydroxide, potassium hydroxide, and lithium hydroxide.

Another component of a Lysis Solution is a complexing salt that confers unique binding properties to nucleic acids (e.g., an RNA-complexing salt), such that the nucleic acids can preferentially bind to a solid support instead of other contaminants such as proteins, phospholipids, etc. In some embodiments, such a complexing salt may be any known complexing salt, such as sodium salt, or lithium salt, such as lithium chloride or lithium bromide. The salt may be present at a concentration of between 3-10 M (e.g., 4 M, 5 M, 6 M, 7 M, 8 M, or 9 M), because preferential binding of DNA and RNA to a solid support is enhanced by high concentrations of alkali-metal salts. In certain embodiments, lithium chloride is used in the Lysis Solution, at a concentration of 4 M.

A Lysis Solution additionally includes one or more amphiphilic reagents. An amphiphilic reagent includes a compound or molecule having a hydrophilic group attached to a hydrophobic functionality, such as a hydrocarbon chain, and having surfactant properties. In some embodiments, the amphiphilic reagent is a detergent. Although anionic, cationic, and zwitterionic detergents may all be used, nucleic acid isolation is optimally achieved through the use of a non-ionic detergent. Although any nonionic detergent may be used, examples of non-ionic detergents are those from the Tween class (Tween-20, Tween-40, Tween-60, Tween-80, etc.), the Triton class (X-100, X-114, XL-80N, etc), Tergitols (XD, TMN-6, etc.) and Nonidets or Igepal (NP-40, etc.). The nonionic detergent may be used at a concentration of 5-15% (e.g., at about 10%, 11%, 12%, 13%, or 14%). In other embodiments, the amphiphilic reagent is a surfactant, such as diethylene glycol monoethyl ether (DGME). The surfactant may be used at a concentration of 5-15% (e.g., 6%, 10%, 11%, 12%, 13%, or 14%). In some instances, a combination of detergents and surfactants may be used. In certain instances, a combination of detergent and surfactant Triton-X and DGME is used. The combination may be at a concentration of 5-15% (e.g., 10%, 11%, 12%, 13%, or 14%). For example, the combination is 5% Triton-X and 5% DGME.

In order to prevent degradation of nucleic acids, such as RNA, nuclease-free water is used in the Lysis Solution. In some embodiments, a chelating agent also may be used to prevent degradation of contaminating nucleic acid. The use of a chelating agent prevents nucleic acid polymers from being degraded to smaller fragments, which may cause additional contamination problems. The chelating agent may be present at a concentration of 1-100 mM (e.g., 2 mM, 5 mM, 8 mM, 10 mM, 15 mM, 20 mM, 25 mM, 35 mM, 45 mM, 50 mM, 65 mM, 75 mM, 85 mM, or 95 mM), or at a concentration of 1-10 mM (e.g., 1.5 mM, 2 mM, 3 mM, 4 mM, 6 mM, 7 mM, or 9 mM). In some instances the chelating agent EDTA is used. In other instances, the chelating agent CDTA is used.

The Lysis Solution of the present invention is advantageous. The unique combination of a high concentration of a complexing salt and a high concentration of a detergent in a neutral- to high-pH buffer inactivates enzymes harmful to nucleic acids (such as RNases), without the use of such reagents as phenol, chloroform, and guanidinium salts. Additionally, the solution confers a high binding property to the nucleic acids such that they tightly bind with the solid support of choice.

(iv) Optional Proteinase K Solution:

In some embodiments, during RNA purification, a user performs an additional Proteinase K step. In some embodiments, during DNA purification, a user performs an additional Proteinase K step. A suitable Proteinase K Solution includes about 10 to 25 mg/mL Proteinase K (e.g., 10 mg/mL, 15 mg/mL, or 25 mg/mL). In certain instances, a suitable Proteinase K Solution has a concentration of 20 mg/mL Proteinase K.

(v) Binding Solution:

The Binding Solution may be used when purifying DNA from a Stabilized Sample in order to improve the binding of DNA to the solid support. The binding may be improved through significant increase in salt concentration, or by dehydration, or both. The present invention features a Binding Solution that has the following components: a buffer, an alkali metal salt, and an amphiphilic reagent, such as a detergent or surfactant or mixture thereof.

The first component of the Binding Solution is a buffer that maintains the pH of the solution. For example, the pH may be at least about 7 (e.g., 7.5, 8, 8.5, 9, or 9.5). The buffer may be used at a concentration of 50-150 mM (e.g., 60 mM, 70 mM, 80 mM, 90 mM, 100 mM, 120 mM, or 140 mM). In some embodiments, Tris buffer is an appropriate buffer. Optionally, a base may be used to adjust the pH of the Binding Solution. The base may be one that can raise the pH of the solutions to no less than 7 (e.g., pH 7.5, pH 8, pH 8.5, or pH 9.0). In some embodiments, the base may be an alkali-metal hydroxide. Such alkali-metal hydroxides include sodium hydroxide, potassium hydroxide, and lithium hydroxide.

Another component of the Binding Solution is a complexing salt that confers unique binding properties to nucleic acids, such that the nucleic acids can preferentially bind to the solid support over other contaminants such as proteins, phospholipids, etc. For example, such a complexing salt may be any known complexing salt, such as a sodium salt or lithium salt, such as lithium chloride or lithium bromide. The salt may be present at a concentration of between 5-15 M (e.g., at about 6 M, 7 M, 8 M, 9 M, 10 M, 11 M, 12 M, 13 M, or at about 14 M) because preferential binding of DNA to a solid support is enhanced by high concentrations of alkali-metal salts.

Another component of the Binding Solution is an amphiphilic reagent. An amphiphilic reagent includes a compound or molecule having a hydrophilic group attached to a hydrophobic functionality, such as a hydrocarbon chain, and having surfactant properties. In some embodiments, the amphiphilic reagent is a detergent. Although anionic, cationic, and zwitterionic detergents may all be used, nucleic acid isolation is optimally achieved through the use of a non-ionic detergent. Although any nonionic detergent may be used, examples of non-ionic detergents are those from the Tween class (Tween-20, Tween-40, Tween-60, Tween-80, etc.), the Triton class (X-100, X-114, XL-80N, etc), Tergitols (XD, TMN-6, etc.) and Nonidets or Igepal (NP-40, etc.). The nonionic detergent may be used at a concentration of 5-15% (e.g., at about 10%, 11%, 12%, 13%, or 14%). In other embodiments, the amphiphilic reagent is a surfactant, such as diethylene glycol monoethyl ether (DGME). The surfactant may be used at a concentration of 5-15% (e.g., 6%, 10%, 11%, 12%, 13%, or 14%). In some instances, a combination of detergents and surfactants may be used. In certain instances, a combination of detergent and surfactant Triton-X and DGME is used. The combination may be at a concentration of 5-15% (e.g., 10%, 11%, 12%, 13%, or 14%). For example, the combination is 5% Triton-X and 5% DGME.

The detergent or surfactant may be anionic, cationic, zwitterionic or nonionic. In one embodiment, a nonionic detergent is used. It has been observed that some charged detergents such as SDS, do not remain solubilized in higher concentration salt solutions and in fact, they may tend to precipitate rather quickly. It is possible however, to use such charged detergents under certain experimental conditions, including but not limited to those described in one embodiment of the present invention, for pre-treating the solid support. Examples of non-ionic detergents include detergents from the Tween, Triton, Tergitol and Nonidet or Igepal classes of detergents. In one embodiment the surfactant is DGME (diethyl glycol monoethyl ether). In certain instances of DNA purification, in order to simplify a kit by reducing the number of reagents, Wash I may be used as a Binding Solution.

(vi) Wash Solutions:

The present invention also teaches of one or more wash solutions that are used to wash the solid support to which nucleic acids are bound, so as to rid it of non-nucleic acid contaminants such as proteins, phospholipids, etc. The wash solutions may contain an alcohol at a concentration greater than 50% (e.g., 60%, 70%, 80%, 90%, 95%, or 100%). The alcohol can be, for example, ethanol or methanol. In some embodiments, ethanol is used at a concentration of 75%. In other embodiments, methanol is used at a concentration of 65%. The Wash I Solution contains a high alkali metal salt concentration, such as a sodium or lithium salt (e.g., lithium chloride or lithium bromide), at a concentration between 4-10 M (e.g., 5-6 M, 4-7 M, 5-8 M, 6-9 M, 6-10 M, 7-10 M, 5 M, 6 M, 7 M, 8 M, 9 M, or 10 M). For the purposes of the present invention, a high salt concentration means a salt concentration high enough to inhibit enzyme activity, to complex to nucleic acid, and to provide a salting-out effect for binding of nucleic acid to the solid phase. The Wash I Solution additionally contains an alcohol (e.g., ethanol or methanol). The alcohol concentration is at 25-80% (e.g., 30-40%, 40-50%, 35-45%, 55-65%, 60-70%, 65-75%, 70-80%, 30%, 40%, 55%, 60%, 70%, or 75%). In some embodiments, Wash I Solution contains ethanol at a concentration of 70%. In other embodiments, Wash I Solution contains methanol at a concentration of 80%.

The Wash II Solution contains a buffer, alcohol, and an optional chelator (e.g., EDTA or CDTA). For purposes of the present invention, the Wash II Solution provides for a final wash to remove any residual biological material. In some embodiments, the buffer composition may be Tris-HCl, such as at pH 6-8 (e.g., pH 6.5, 7 or 7.5). The buffer concentration may be at 50-150 mM (e.g., 60 mM, 70 mM, 80 mM, 90 mM, 100 mM, 120 mM, or 140 mM). The Wash II Solution may additionally contain an alcohol (e.g., ethanol or methanol). The alcohol concentration may be at 50-90% (e.g., 55-65%, 60-70%, 65-75%, 70-80%, 55%, 60%, 60%, 75%, 80%, or 85%). The EDTA concentration may be at 1-20 mM (e.g., at 5-10 mM, 7-15 mM, 10-17 mM, 15-20 mM, 2 mM, 4 mM, 6 mM, 7 mM, 8 mM, 9 mM, 10 mM, 11 mM, 12 mM, 13 mM, 15 mM, 17 mM, or 19 mM). In certain instances, Wash II contains ethanol at a concentration of 80%, and EDTA at a concentration of 8 mM. In other instances, Wash II contains ethanol at a concentration of 70%, and EDTA at a concentration of 10 mM. In certain embodiments, Wash II contains methanol at a concentration of 60%, and EDTA at a concentration of 12 mM. In other embodiments, Wash II contains methanol at a concentration of 75%, and EDTA at a concentration of 9 mM.

DNA removal may be desired or even critical for certain applications that require isolated RNA. DNase digestion, using the DNase Wash Solution of the present invention, has proven to be an effective method for removing DNA contamination from RNA samples. The DNase Wash Solution contains an alcohol (e.g., ethanol or methanol), salt, and a chelating agent (e.g., EDTA or CDTA). The alcohol concentration may be at 10-50% (e.g., at 10-30%, 20-40%, 30-50%, 15%, 20%, 25%, 30%, 35%, or 45%). In some embodiments, the alcohol may be ethanol at a concentration of 50%. In certain embodiments, the DNase Wash Solution may contain a salt, such as a lithium salt (e.g., lithium chloride, lithium bromide). The lithium salt concentration may be at 2-5 M, (e.g., 3-4 M, 2 M, 3 M, 4 M, or 5 M). In some instances, the DNase Wash Solution may contain lithium chloride at a concentration of 4 M. In certain embodiments, the formulation may further contain a chelating agent. In certain instances, the chelating agent may be EDTA. In other instances, the chelating agent may be citrate. The chelating agent may be at a concentration of 25-100 mM (e.g., 30-70 mM, 40-80 mM, 50-90 mM, 35 mM, 45 mM, 50 mM, 60 mM, 75 mM, 85 mM, or 95 mM trisodium citrate). In some embodiments, a DNase Wash Solution contains ethanol at a concentration of 30%, LiCl at a concentration of 4M, and EDTA at a concentration of 50 mM. In other embodiments, a DNase Wash Solution contains ethanol at a concentration of 40%, LiCl at a concentration of 5M, and EDTA at a concentration of 65 mM.

(vii) Elution Solutions:

Substantially undegraded nucleic acids (e.g., DNA or RNA) that are bound to the solid support as a result of the isolation procedure can be eluted using an Elution Solution. The simplicity of the reagents used in lysing the biological material and binding of the nucleic acid to the solid support, and in washing the solid support taught by the present invention lends itself to a simple Elution Solution. A variety of Elution Solutions are known to those having ordinary skilled in the art. In some embodiments, Versagene™ DNA Elution Solution (Gentra Systems, Inc., Minneapolis, Minn.) may be used for eluting bound substantially undegraded DNA. In some instances, Tris-EDTA (TE) may be used for eluting bound substantially undegraded DNA.

Substantially undegraded RNA, which is bound to the solid support, may be eluted using an RNA Elution Solution. In some instances, Versagene™ RNA Elution Solution (Gentra Systems, Inc., Minneapolis, Minn.) may be used for eluting bound substantially undegraded RNA. In certain embodiments, RNase-free water may be used to elute bound substantially undegraded RNA. In other embodiments, water may be treated with a substance that inactivates RNases, such as diethyl pyrocarbonate (DEPC), and used for eluting RNA. Other RNA Elution Solutions known to those having ordinary skill in the art also may be used. For example, Gentra Solid Phase RNA Elution Solution (Gentra Systems, Inc., Minneapolis, Minn.) may be used.

Solid Support

A variety of solid supports may be used in the present invention. Suitable solid supports include, for example, silica-based supports such as glass fiber, or other materials such as cellulose, cellulose acetate, nitrocellulose, nylon, polyester, polyethersulfone, polyolefin, polyvinylidene fluoride, and combinations thereof. In some embodiments, the solid support may be encased or immobilized in a vessel to enable plug-flow or continuous-flow DNA isolation methods. In other embodiments, the material of the solid support may be packed so as to create a freestanding solid support such as a membrane, disk, or cylinder that may be immobilized or encased in a suitable vessel, such as a tube or plate. In some embodiments, the solid support may be fibrous or particulate to allow optimal contact with a biological material. The size of the solid support suitable for use with the reagents of this invention may vary according to the volume of the material (e.g., a biological material). For example, glass fiber membranes may be cut to different sizes, in order to allow for the binding, purification and elution of different quantities of DNA.

The shape of the solid support suitable for use with the reagents of this invention may be, for example, a sheet, a precut disk, cylinder, single fiber, or a solid support composed of particulates. The material of the solid support may be packed so as to create a freestanding solid support such as a membrane, disk, or cylinder that may be immobilized or encased in a suitable vessel. If necessary, the solid support is contained in an appropriate vessel, e.g., a paper form (such as a Guthrie card), a microcentrifuge tube, a spin tube, a 96-well plate, a chamber, or a cartridge. An example is Whatman D glass fiber membrane within a basket and placed inside a 2 mL microfuge tube. If a solid support has fibers, it may be encased in a suitable vessel so as to pack the fibers appropriately, allow for optimal nucleic acid binding, and the washing away of contaminants such as protein, phospholipids, etc.

In some instances, the solid support may be pre-treated with an RNase solution in order to degrade RNA present in the sample (e.g., a biological sample). In other instances, purification may be improved by the use of RNase-treated columns (such as the ones offered by Gentra Systems, Inc., Minneapolis, Minn.). The RNase-treated columns degrade RNA that is present in a sample (e.g., a biological sample). Additionally, using the pre-treated columns eliminates the need for a separate RNase digestion step, as is required in some DNA isolation methods. In some embodiments of RNA isolation, a DNA Lysis Solution may be added directly to the material used in making the solid support (e.g., fibers, etc.), and may be allowed to dry before it is made into the final user-ready form (e.g., paper, swab, disk, plug, column, etc.).

Purification/Isolation Methods

The present invention also provides methods for purifying DNA, or RNA, or both, from material (e.g., biological material) that has been preserved in stabilization reagents ("Stabilized Sample"), including reagents employed under the trade names of Paxgene™, RNAsafer®, RNAlater®, and Tempus™ solutions. The reagents and solid supports taught in the invention lend themselves to alternate isolation methods.

In some embodiments a diluent is added to the biological material in the presence of the stabilization reagent to facilitate preparation of a crude lysate prior to further purification of the Stabilized Sample.

In some embodiments, a Stabilized Sample is contacted with a Solubilization Solution before it is contacted with a Lysis Solution. In other instances, where the stabilization reagent completely lyses and solubilizes the nucleic acid in a sample, a Solubilization Solution may not be required.

In some embodiments, the Lysis Solution and the Solubilization Solution may be combined.

In some instances, a Lysis Solution is contacted with a Stabilized Sample before the sample is contacted with a solid support. The Lysis Solution is used to lyse the material (e.g., biological material) and release nucleic acids into a lysate, before adding the lysate to the solid support. Additionally, the Lysis Solution prevents the deleterious effects of harmful enzymes such as nucleases. The Lysis Solution volume may be scaled up or down depending on the volume of the Stabilized Sample. Once the Stabilized Sample is lysed, the lysate is then added to the solid support. In other instances, the Lysis Solution may be added directly to the solid support, thereby eliminating a step, and further simplifying the method. In this embodiment, the Lysis Solution may be applied to the solid support and then dried on the solid support before contacting the Stabilized Sample with the pre-treated solid support.

Enzymes such as RNase and DNase may be added either directly to the solid support to pre-treat the column, or added to the Lysis Solution to degrade contaminating RNA or DNA present in the sample. Using the pre-treated columns with Lysis and/or RNase or DNase eliminates the need for a separate lysis and/or nuclease digestion steps, as is typically required in conventional methods.

In some embodiments of purifying DNA, following lysis, the binding of the nucleic acid to the solid support can be improved by employing a Binding Solution. The binding may be improved through significant increase in salt concentration, by dehydration, or by both.

Following lysis and binding of the nucleic acids, any remaining biological material is optionally removed by suitable means such as centrifugation, pipetting, pressure, vacuum, or by a combined use of these means with a Wash Solution, such that the nucleic acids are left bound to the solid support. In some instances, the wash steps may be repeated depending on the tenaciousness of the sample type and amount of non-nucleic acid biological material in the sample. The remainder of the non-nucleic acid biological material, which includes proteins, phospholipids, etc., may be removed first by centrifugation. By doing this, the unbound contaminants are separated from the solid support. The wash steps rid the solid support of substantially all contaminants, and leave behind nucleic acid preferentially bound to the solid support.

Subsequently, bound nucleic acids may be eluted using an adequate amount of an Elution Solution known to those having ordinary skill in the art. The solid support may then be centrifuged, or subjected to pressure or vacuum, in order to release the nucleic acid from the solid support, and can then be collected in a suitable vessel.

FIG. 1 is a flow diagram depicting a procedure to isolate DNA, RNA, or both, from a sample using the present invention. In some embodiments, users may perform isolation of only DNA from a sample according to the methods featured in the invention. In other embodiments, users may perform isolation of only RNA according to the methods featured in the invention. In some instances, users choosing to perform isolation of both RNA and DNA from the same sample would divide the sample following its collection. In other instances, users choosing to perform isolation of both RNA and DNA from the same sample would divide the sample following a solubilization step.

Articles of Manufacture

The reagents, methods and kits featured in the present invention provide substantially pure and undegraded nucleic acids with relatively little contaminating impurities such that the nucleic acids may be used in downstream processes known to those having ordinary skill in the art. The invention features, inter alia, a kit that includes specific protocols, which in combination with the reagents and optionally the solid supports described herein, may be used for purifying DNA, RNA, or both DNA and RNA from samples according to the methods of the invention. Substantially pure, undegraded nucleic acids are nucleic acids that is suitable for use in subsequent analyses, including, but not limited to, nucleic acid quantification, restriction enzyme digestion, DNA sequencing, hybridization technologies, such as Southern Blotting, etc., amplification methods such as Polymerase Chain Reaction (PCR), Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), Quantitative PCR (qPCR), or other DNA analyses, as well as RT-PCR, in vitro translation, Northern blotting, microarray analysis and other RNA analyses.

This invention will be further described by reference to the detailed examples included herein. These examples are offered to further illustrate the various specific and illustrative embodiments and techniques. It should be understood, however, that many variations and modifications may be made while remaining within the scope of the present invention.

EXAMPLES

Example 1—RNA Purification from PreAnalytix™ Paxgene™ Blood Collection Tubes

Blood samples were collected from donors into Paxgene™ Collection Tubes (PreAnalytiX™, Valencia, Calif.). Samples were treated essentially according to the manufacturer's instructions. Samples were centrifuged at 3000×g for 10 minutes. The resulting sample pellet obtained upon centrifugation of a Paxgene™ RNA Collection Tube was a water-insoluble precipitation of total nucleic acid, negatively charged protein, and the cationic surfactant Catrimox™. The pellet was washed of gross blood product contamination. Five mL of water were added to the pellet and the sample was vortexed rapidly. The tube was subsequently centrifuged again at 3000×g for 10 minutes, and the supernatant was decanted to obtain a cleaner pellet.

The resulting sample pellets were not readily soluble in the Lysis Solution (6 M LiCl, 5% Triton X-100, 5% DGME, 10 mM EDTA, 100 mM TRIZMA, pH 8.8), and therefore a Solubilization Solution was used. One-hundred and fifty µl of Solubilization Solution (38 mM TRIZMA base, 12 mM TRIZMA HCl, 10 mM EDTA, 5% Triton X-100) were added to the sample. Resuspending the pellet in water or Tris helped solubilize the pellet in the Lysis Solution in most, but not all embodiments. For example, blood donors with high or abnormal protein levels would fail this RNA isolation due to increased protein contamination. However, adding a non-ionic, fully compatible detergent (Triton X-100) to the Solubilization Solution completely solubilized the pellet. This suspension, when added to Lysis Solution allows the RNA to bind to the solid support without protein contamination failure. The buffer component of the Solubilization Solution was found to play a critical role. The Paxgene™ RNA Collection Tube preserves RNA with a low pH component to inhibit enzymatic degradation. RNA binding to the solid support of the present invention in Lysis Solution optimally takes place at pH 8.5-9.5. In this example, the low pH of the pellet lowers the overall pH of the Solubilization Solution, in some embodiments out of this optimal range and also favors protein binding. Therefore, adding a volume of buffer at the correct binding pH absorbs any trace acidic carryover from the pellet and allowed the isolation process to proceed without failure. It is recognized that the pH of the buffer of the Solubilization Solution, therefore, may require adjustment depending on the pH of the pellet carried over for the Stabilized Sample.

Three-hundred μl of Lysis Solution were added to the sample and mixed with each sample. In this instance, the pellet did not require lysis, but the Lysis Solution formulation (6 M LiCl, 5% Triton X-100, 5% DGME, 10 mM EDTA, 100 mM TRIZMA, pH 8.8) facilitated binding the target molecules to the solid support. Ten μL of a Proteinase K Solution were added to each sample and each sample was incubated for 15 minutes at on ice. The entire sample was added to the Binding Column (Whatman D glass fiber membrane within a basket and placed inside a 2 mL microfuge tube) and centrifuged >13,000×g for 1 minute. Four-hundred μL of Wash I Solution (5 M LiCl, 55% ethanol) were added to each sample and each sample was centrifuged >13,000×g for 2 minutes. Next, 50 μL of DNase Wash Solution were added and each sample was incubated for 15 minutes at room temperature. Two-hundred μL of DNase Wash Solution (30% ethanol, 3.5 M LiCl, 50 mM trisodium citrate) were added and centrifuged >13,000×g for 1 minute. Another 200 μL of DNase Wash Solution were added and each sample was centrifuged >13,000×g for 1 minute, followed by an addition of 200 μL of Wash II Solution (70% ethanol, 5 mM EDTA, 100 mM Tris, pH 7) and centrifugation at >13,000×g for 1 minute. This last step was repeated once. Finally, 50 μL of DEPC-treated water were added to the column in order to elute the RNA.

In order to test the quality of the RNA obtained by the method described above, purified and resuspended RNA was loaded onto a 1% agarose gel and subjected to separation. RNA obtained by the above method was intact and essentially free of DNA.

Example 2—DNA Purification from PreAnalytix™ Paxgene™ Blood Collection Tubes

Blood samples were collected from donors into Paxgene™ Collection Tubes (PreAnalytiX™, Valencia, Calif.). Samples were treated essentially according to the manufacturer's instructions. Samples were centrifuged at 3000×g for 10 minutes. The resulting sample pellet obtained upon centrifugation of a Paxgene™ RNA Collection Tube was a water-insoluble precipitation of total nucleic acid, negatively charged protein, and the cationic surfactant Catrimox™. The pellet was washed of gross blood product contamination. Five mL of water were added to the pellet and the sample was vortexed rapidly. The tube was subsequently centrifuged again at 3000×g for 10 minutes, and the supernatant was decanted to obtain a cleaner pellet.

One hundred μL of Solubilization Solution (38 mM TRIZMA base, 12 mM TRIZMA HCl, 10 mM EDTA, 5% Triton X-100, 2 μl of 4 mg/mL RNAse A) was added to the samples. The samples were vortexed to solubilize. Two hundred μL of Lysis Solution (6 M LiCl, 5% Triton X-100, 5% DGME, 10 mM EDTA, 100 mM TRIZMA, pH 8.8) and 10 ul Proteinase K Solution were added to the samples, vortexed to mix, and incubated for 15 minutes on ice. To the samples was added either 300 μL of Binding Solution (10 M LiCl, 10% DGME, 100 mM Tris) or 300 μL of Wash I Solution (5 M LiCl, 55% ethanol). Both solutions allowed genomic DNA to bind to the glass fiber solid support. The bound DNA was washed once with 400 μL of Wash I Solution (5 M LiCl, 55% ethanol), and twice with 200 μL with Wash II Solution (70% ethanol, 5 mM EDTA, 100 mM Tris, pH 7). The DNA was subsequently eluted in TE buffer (Tris-EDTA).

In order to test the quality of the DNA obtained by the methods described above, purified and resuspended DNA was loaded onto a 1% agarose gel and subjected to electrophoresis separation.

Taken together, the results demonstrate that both DNA and RNA can be prepared using the methods of the present invention from a single tube of blood collected using Paxgene™ RNA collection tubes from PreAnalytiX™.

Example 3—RNA Purification from Applied Biosystems Tempus™ Blood Collection Tubes Three mL of blood was drawn from donors into Tempus™ tubes and mixed at <25° C. The manufacturer's directions were followed: The sample was decanted into a 50 mL tube and diluted with 3 mL of Phosphate Buffered Saline (PBS) and vortexed to mix, then centrifuged at 2000×g for 30 minutes at 4° C.

The resulting pellet was not easily visible, but is soluble directly within the Lysis Solution and can be added directly to the glass fiber solid support without any other binding reagents. The pellet was solubilized by the addition of 300 μL of Lysis Solution (6 M LiCl, 5% Triton X-100, 5% DGME, 10 mM EDTA, 100 mM TRIZMA, pH 8.8, plus 3 μL TCEP) and vortexed 60 seconds. The samples were added to the Binding Column and centrifuged at 3000×g for 60 seconds. The samples were transferred to a new tube. The RNA was washed by adding 400 μL Wash I, spinning at 3000×g for 30 seconds. The technology of the Tempus™ collection tube alleviates the need for any DNAse treatment. Therefore, the samples were washed by adding 200 μL Wash II and spinning at 3000×g for 30 seconds. 200 μL Wash II was added and the samples spun at 3000×g for 120 seconds. 50 μL of RNase-free water was added to elute the RNA and the samples were spun at 3000×g for one minute.

This protocol generates total RNA yields equal or better to an equivalent volume of blood collected in EDTA tubes or Paxgene collection tubes and isolated with the procedure in Examples 1 and 2 or using Paxgene™ RNA Purification protocol for blood.

Example 4—RNA Purification from Applied Biosystems Tempus™ Blood Collection Tubes Using Ethanol Three mL of blood was drawn from donors into Tempus™ tubes, which contain about 6 ml of the Tempus™ stabilizing agent, and mixed at <25° C. Samples were incubated at room temperature for about two hours. The sample was then decanted into a 50 ml tube, and 3 ml of 95% ethanol was added, to yield a total volume of about 12 ml. The tube was vortexed for about 120 seconds, and then centrifuged at 6000×g for 30-60 minutes. The supernatant was decanted, and the tube inverted for about 120 seconds to dry the cell pellet.

The pellet was solubilized by the addition of 300 µL of Lysis Solution (6 M LiCl, 5% Triton X-100, 5% DGME, 10 mM EDTA, 100 mM TRIZMA, pH 8.8, plus 3 µL TCEP) and vortexed 60 seconds. The samples were added to the Binding Column and centrifuged at 3000×g for 60 seconds. The samples were transferred to a new tube. The RNA was washed by adding 400 µL Wash I, spinning at 3000×g for 120 seconds. Fifty µL of DNAse (25 U/50 µL) was added, and allowed to incubate at room temperature for about 15 minutes. Next, 200 µL of DNAse wash (3.5 M Lithium Chloride, 50 mM Sodium Citrate and 30% Ethanol) was added, and the tube is centrifuged at 3000×g for 60 seconds. The supernatant was decanted and 200 µL Wash II solution is added, followed by spinning at 3000×g for 60 seconds. 200 µL Wash II was added and the samples spun at 3000×g for 120 seconds. 50 µL of Elution Solution (Nuclease free water, or Diethylpyrocarbonate treated water or 10 mM Tris, 0.1 mM EDTA, pH 7.5) was added to elute the RNA and the samples were spun at 3000×g for one minute.

FIG. 2 shows that adding ethanol in lieu of PBS (as in Example 3) in the initial dilution step allows a much greater yield of RNA to be recovered at a lower centrifugation speed. Maximal yields in PBS required a centrifugation speed of 5500×g while similar yields can now be obtained at 3000×g in ethanol. 3000×g is a much more common centrifuge speed commonly found in laboratories.

Figure 3:
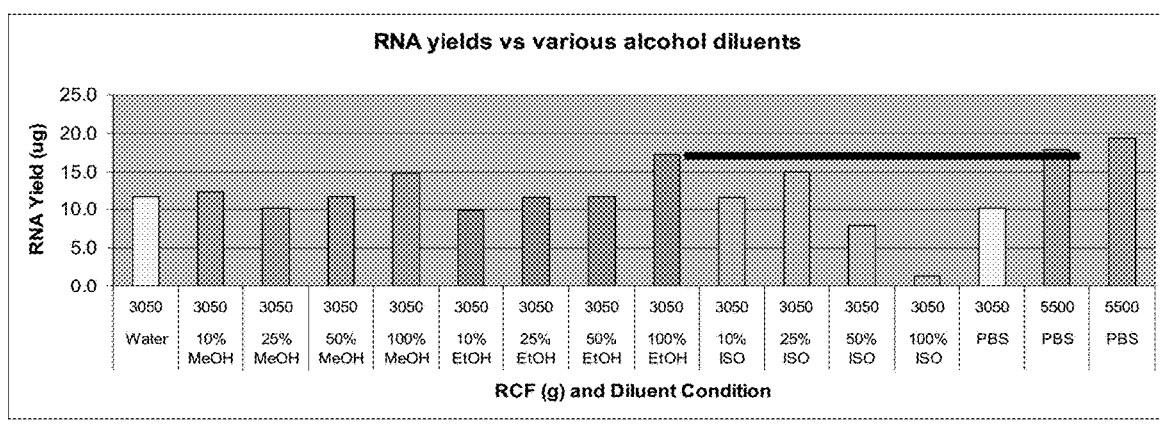

The inventors also tested different concentrations of alcohol as a Diluent in this method. The results are shown in FIG. 3. The graph shows yields obtained when using different concentrations of alcohols as a diluent. All tubes had the following:

3 mL whole blood
6 mL Tempus™ tube stabilizing agent
3 mL Diluent

Using the faster 5500×g centrifugation with PBS as a baseline, one can see that similar yields of RNA can be obtained at lower centrifugation speeds when diluting in 100% Ethanol or 100% Methanol. Ethanol is chosen in certain embodiments, as it is much more commonly found in biotech laboratories. High concentrations of Isopropanol tend to precipitate and fail the isolation.

Figure 4:
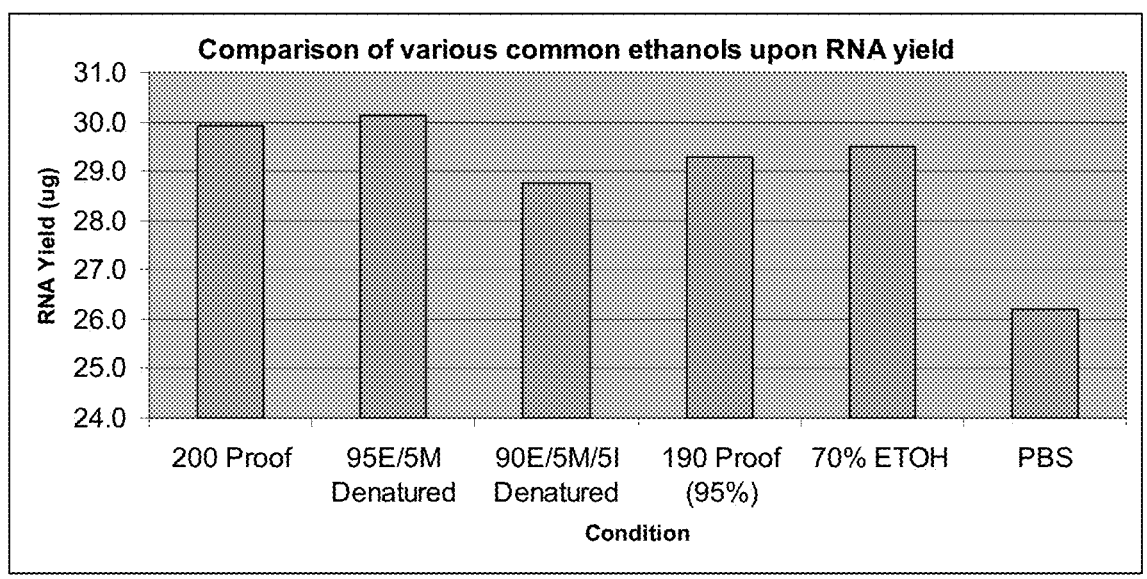

Many reagent-grade ethanol preparations are denatured with 5% Methanol and/or 5% Isopropanol in order to avoid liquor licensing and taxation. Many ethanol preparations are also commonly purchased at 95% concentration (balance water) as opposed to 100% purity. 70% ethanol is also a common laboratory concentration. The graph depicted in FIG. 4 shows that there was no effect when changing to any of these subtle formulation differences.

A number of embodiments of the invention have been described. Nevertheless, it will be understood that various modifications may be made without departing from the spirit and scope of the invention. Accordingly, other embodiments are within the scope of the following claims.

What is claimed is:

1. A method for isolating RNA from a test sample containing RNA, comprising:
    (a) contacting a pellet obtained from a test sample that is stabilized with a cationic detergent with a Solubilization Solution comprising a buffer at a concentration of 10-20 mM and at a pH between about 7 and 9, a base at a concentration of 20-50 mM, and an amphiphilic reagent to form a mixture;
    (b) subsequently contacting the mixture from step (a) with a Lysis Solution buffered at a pH of greater than about 7 to create an isolation sample, wherein the Lysis Solution comprises a lithium salt at a concentration between 3 and 10 M, a buffer, and an amphiphilic reagent, but is free of guanidinium salts and urea, wherein the Lysis Solution is different from the Solubilization Solution;
    (c) contacting the isolation sample to a solid support such that nucleic acids comprising RNA in the isolation sample bind to the solid support;
    (d) washing the solid support with one or more Wash Solutions to remove materials other than bound nucleic acids comprising RNA; and
    (e) eluting the bound RNA from the solid support in order to obtain RNA.

2. The method of claim 1, wherein the buffer in the Solubilization Solution is Tris HCl.

3. The method of claim 1, wherein the amphiphilic reagent in the Solubilization Solution is a detergent.

4. The method of claim 3, wherein the detergent is a non-ioninc, anionic, cationic or zwitterionic detergent.

5. The method of claim 4, wherein the non-ionic detergent is from the Tween class, Triton class, Tergitols, Nonidets or Igepal.

6. The method of claim 5, wherein the detergent is present at a concentration of about 5 to 15%.

7. The method of claim 1, wherein the Solubilization Solution further comprises a chelator.

8. The method of claim 7, wherein the chelating agent is ethylenediaminetetraacetic acid (EDTA).

9. The method of claim 8, wherein the chelating agent is present at a concentration of about 1 to 20 mM.

10. The method of claim 1, wherein the buffer in the Lysis Solution is Tris-HCl.

11. The method of claim 1, wherein the pH of the Lysis Solution is at least about 8.

12. The method of claim 1, wherein the pKa of the buffer in the Lysis Solution is at least about 8.

13. The method of claim 1, wherein the buffer in the Lysis Solution is present at a concentration of about 50 to 150 mM.

14. The method of claim 1, wherein the Lysis Solution further comprises a base.

15. The method of claim 14, wherein the base is alkali-metal hydroxide.

16. The method of claim 15, wherein the alkali-metal hydroxide is sodium hydroxide, potassium hydroxide, or lithium hydroxide.

17. The method of claim 1, wherein the lithium salt is lithium chloride or lithium bromide.

18. The method of claim 1, wherein the amphiphilic reagent in the Lysis Solution is a detergent.

19. The method of claim 18, wherein the detergent is a non-ioninc, anionic, cationic or zwitterionic detergent.

20. The method of claim 19, wherein the non-ionic detergent is from the Tween class, Triton class, Tergitols, Nonidets or Igepal.

21. The method of claim 18, wherein the detergent is present at a concentration of about 5 to 15%.

22. The method of claim 1, wherein the amphiphilic reagent in the Lysis Solution is a surfactant.

23. The method of claim 22, wherein the surfactant is diethylene glycol monoethyl ether (DGME).

24. The method of claim 22, wherein the surfactant is present at a concentration of about 5 to 15%.

25. The method of claim 1, wherein the amphiphilic reagent is a combination of one or more detergents and/or one or more surfactants.

26. The method of claim 1, wherein the Lysis Solution further comprises a chelating agent.

27. The method of claim 26, wherein the chelating agent is present at a concentration of about 1 to 100 mM.

28. The method of claim 26, wherein the chelating agent is EDTA or CDTA.

29. The method of claim 1, further comprising contacting the sample with a Proteinase K Solution comprising Proteinase K.

30. The method of claim 29, wherein the Proteinase K is present at a concentration of about 10 to 25 mg/mL.

31. The method of claim 1, wherein the alcohol in the one or more Wash Solutions is present at a concentration greater than 50%.

32. The method of claim 1, wherein the alcohol in the one or more Wash Solutions is ethanol or methanol.

33. The method of claim 1, wherein a first Wash Solution (Wash Solution I) contains an alkali metal salt at a concentration of about 4 to 10M.

34. The method of claim 33, wherein the alkali metal salt is a sodium or lithium salt.

35. The method of claim 34, wherein the alkali metal salt is lithium chloride or lithium bromide.

36. The method of claim 33, wherein the Wash Solution I further comprises an alcohol at a concentration of about 25 to 80%.

37. The method of claim 36, wherein the alcohol is ethanol or methanol.

38. The method of claim 1, wherein a second Wash Solution (Wash Solution II) comprises a buffer at a pH of about 6 to 8 and an alcohol at a concentration of about 50 to 90%.

39. The method of claim 38, wherein the alcohol is ethanol or methanol.

40. The method of claim 38, wherein the buffer is Tris-HCl at a concentration of about 50 to 150 mM.

41. The method of claim 38, further comprising a chelator.

42. The method of claim 41, wherein the chelator is EDTA or CDTA at a concentration of about 1 to 20 mM.

43. The method of claim 1, wherein one or more Wash Solutions is a DNase Wash Solution comprises an alcohol at a concentration of about 10 to 50%, an alkali metal salt at a concentration of about 2 to 5 M, and a chelating agent at a concentration of about 25 to 100 mM.

44. The method of claim 43, wherein the alcohol is ethanol or methanol.

45. The method of claim 43, wherein the chelating agent is EDTA, CDTA or citrate.

46. The method of claim 43, wherein the alkali metal salt is a lithium salt.

47. The method of claim 46, wherein the lithium salt is lithium chloride or lithium bromide.

48. The method of claim 1, wherein the solid support comprises components of silica, cellulose, cellulose acetate, nitrocellulose, nylon, polyester, polyethersulfone, polyolefin, or polyvinylidene fluoride, or combinations thereof.

* * * * *